United States Patent [19]

Hyman

[11] Patent Number: 4,673,637
[45] Date of Patent: Jun. 16, 1987

[54] METHOD FOR DETECTING BACTERIA IN URINE AND FOR TREATING RHEUMATOID ARTHRITIS, ESSENTIAL HYPERTENSION AND OTHER DISEASES ASSOCIATED WITH BACTERIURIA

[76] Inventor: Edward S. Hyman, 3420 Jefferson Ave., New Orleans, La. 70125

[21] Appl. No.: 603,088

[22] Filed: Apr. 23, 1984

[51] Int. Cl.$^4$ .......................... C12Q 1/04; G01N 1/00
[52] U.S. Cl. ........................................ 435/34; 435/29; 435/39; 435/825; 435/18; 436/501; 436/175; 436/177; 436/178; 424/3
[58] Field of Search .................... 435/29, 34, 39, 825, 435/18; 436/175, 177, 178; 424/3

[56] References Cited

U.S. PATENT DOCUMENTS

| | | | |
|---|---|---|---|
| 4,073,694 | 2/1978 | Buda et al. | 435/29 X |
| 4,094,745 | 6/1978 | Scholefield | 435/34 X |
| 4,225,669 | 9/1980 | Melnick et al. | 435/29 |
| 4,273,867 | 6/1981 | Lin et al. | 436/825 X |

OTHER PUBLICATIONS

Conn, H. F., ed., Current Therapy, (1966), W. B. Saunders Co., pp. 392–395.
Dumonde, D. C. ed., Infection and Immunology in the Rheumatic Diseases, Blackwell Sci. Pub., 1976, pp. 95–186, 187–287, 627–640.
McCarty, D. J., ed., Arthritis and Allied Conditions, 1979, Lea & Febiger Pub., pp. 417, 491–499.
Petersdorf, R. G., et al., eds., Principles of Internal Medicine, Tenth Edition, (1983), McGraw-Hill, Pubs., pp. 345–347.
Kaplan, et al., eds., Clinical Hypertension, Third Edition, (1982), Williams & Wilkins Pubs.
Utsinger, et al., eds., Rheumatoid Arthritis, J. B. Lippincott Pubs., 1985, pp. 11–17.

*Primary Examiner*—Christine E. Nucker
*Assistant Examiner*—Stephen C. Wieder
*Attorney, Agent, or Firm*—H. P. Settle

[57] ABSTRACT

A novel method of urine specimen preparation comprising intense centrifugation and a lipid wash mitigates or prevents loss of bacteria-containing sediment prior to examination. Modifications of the method facilitate examination of urines with interfering constituents such as glucose, phosphates, and soluble and insoluble proteins. By this method, bacteria have been found in the urine of patients suffering from rheumatoid arthritis and essential hypertension. These bacteria were not detected in standard urine preparations. Administration of antibiotic agents effective against the bacteria detected, such as clindamycin, destroyed these bacteria and provided therapeutic relief.

19 Claims, 2 Drawing Figures

METHOD FOR DETECTING BACTERIA IN URINE AND FOR TREATING RHEUMATOID ARTHRITIS, ESSENTIAL HYPERTENSION AND OTHER DISEASES ASSOCIATED WITH BACTERIURIA

This invention relates to a new method of detecting abnormal levels of bacteria in urine, and to new methods for the treatment of patients suffering from rheumatoid arthritis, essential hypertension, and other diseases in which significant bacteriuria was detected by the novel specimen preparation of the present invention that would not have been easily demonstrated by known procedures.

BACKGROUND OF THE INVENTION Under good conditions bacteria may be seen in an aqueous medium under the microscope at as low as 100 diameters magnification, but they are usually visualized at 1000 diameters magnification after drying and staining with appropriate dyes. Both methods of visualization have been used to examine urine. Much more commonly bacteria are demonstrated in urine by allowing them to grow in an appropriate culture medium until the colonies are visible to the naked eye.

By counting the colonies and multiplying by the dilution of the urine, and by assuming that one colony represents a single bacterium in the original specimen, the number of bacteria in a cubic centimeter of urine may be estimated.

The direct microscopy and the culture methods each have pitfalls In the past 20-25 years the direct visualization of bacteria in urine has largely been abandoned in favor of the methods involving culturing and counting the colonies of bacteria. Indeed virtually all of the studies of the significance of bacteriuria are based upon culturing the urine, and the direct microscopic examination of urine has been relegated to the status of a quick but inadequate screening procedure which may be helpful because it can be correlated with the culture methods.

Figure 1:
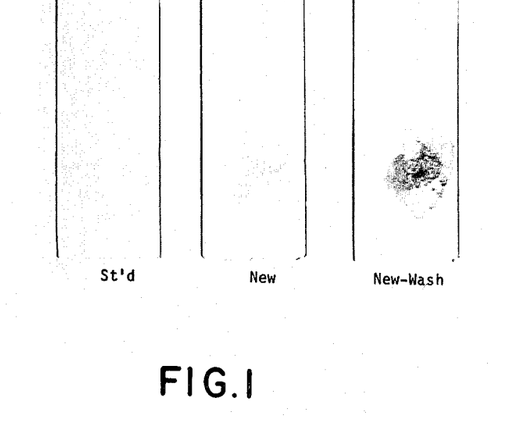
FIG. 1 Shows the loss of sediment in the standard method compared to the new method, and the improvement achieved by modifying the new method as taught herein to include a saline wash.
Figure 2:
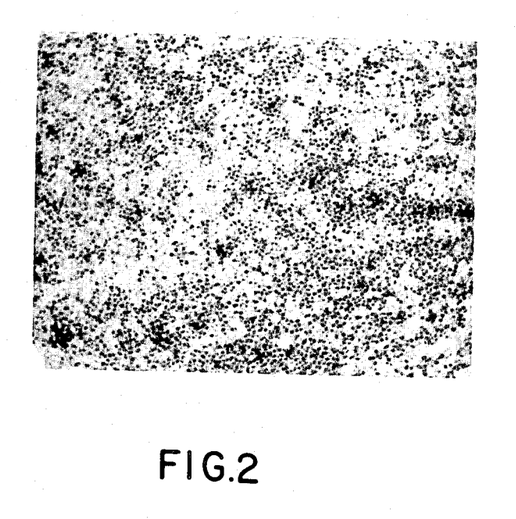
FIG. 2 Shows innumerable cocci in a smear of sediment of a urine that was negative by culture.

Any culture method requires that the bacteria will grow in the laboratory in the medium selected and in the time allotted. If the bacteria are damaged or dead when they left the body, then they will not grow There are many reasons why bacteria in urine would be damaged. The ionic strength or osmolality of the solution may be damaging. The oxidation potential of urine is usually too high (e.g., +0.22 to +0.25 volts). There may be a noxious metabolite in urine. (Human antibodies have been identified in urine and they have been demonstrated to be deposited on bacteria in urine.) Any or many of these factors may render a given bacterium non-viable in vitro. Finally, if the medium used is inappropriate for the growth of the particular organisms present, they will not grow. It can be readily shown by staining and microscopy that many of the bacterial forms found under the microscope were not alive at the time the specimen was obtained. For example, some do not contain nucleic acid, a biochemical component essential to life. Should all of the bacteria in a given specimen be devoid of nucleic acid, then none will grow and the culture of urine remains sterile. Indeed many urine specimens from sick patients containing huge numbers of bacteria will not yield a thriving bacterial culture in the hospital bacteriology laboratory. When the laboratory reports "no growth" the clinician may abandon the possibility of significant bacteriuria, and hence the possibility of an infectious cause. Nonetheless, these dead, damaged or fastidious bacteria, though they do not grow in culture, may in vivo have caused or exacerbated the patient's illness. FIG. 2 shows innumerable small cocci found, using the novel method taught herein, in the urine of a patient for whom the attempt to demonstrate bacteriuria by culture technique was completely unsuccessful. With regard to the direct examination of the urine, it must be noted that although bacteria may be seen in urine at only 100 diameters magnification, the size of the image is not the only consideration. Should the optical density and refractive index of a dead bacterium be near that of the medium, then it would not be detected by ordinary light microscopy. It may be seen by staining or perhaps by some specialized lighting. (Even then, as pointed out by Kunin, round bacteria cannot be distinguished from other near round particles such as crystals.) In my method the urine is examined wet at 100 to 400 diameters magnification, but it is also dried and prepared in a particular way so as to retain and preserve the bacterial structure through staining. In particular, I have found that urine contains lipids which act as detergents. Should they be allowed to remain on the slide when an aqueous dye is applied to the slide, then much of the sediment (including bacteria) will wash off of the slide and the preparation will be lost. This is a major reason why past attempts to study bacteriuria have failed. The photograph of FIG. 1 illustrates the difference. In that photograph one slide had been prepared in the standard way and the other has been washed with a lipid solvent. After staining much more sediment is found on the washed slide. Most of the sediment had washed off in the standard preparation. A chromatogram of the lipids removed reveals several lipids in the range of polarity of the phospholipids (e.g., lecithin, phosphatidylserine, etc. which substances act as detergents) but they do not contain appreciable phosphorus and thus they are not phospholipids. Standard methods of preparing and staining urine specimens, such as that of Melnick, U.S. Pat. No. 4,225,669, do not provide for the precautionary removal of these lipids.

Rheumatoid arthritis (RA) is a chronic inflammation of the joints, generally regarded as a systemic autoimmune disorder. Its etiology is unknown, but it has been postulated that it is associated with microbial infection. See, e.g., D. C. Demonde, ed., Infection and Immunity in the Rheumatic Diseases, 95-287 (Blackwell Scientific Publications, London: 1976). The evidence, however, until the present discovery, was inconclusive. See, e.g., D. J. McCarty, et al., ed., Arthritis and Allied Conditions: A Textbook of Rheumatology, ch 28 at 417 (9th ed. 1979); R. G. Petersdorf, et al., ed., Harrison's Principles of Internal Medicine, Part Six, Chapter 346, at 1977 (McGraw Hill: 1983). Bacteriuria has not been associated with RA, and indeed one authority remarks "Urinary abnormalities are relatively uncommon in RA . . . Urinary tract infection was not found to be increased in RA patients." McCarty, supra, chapter 33, page 499, citing Ann. Rheum. Dis., 27: 345 (1968). Hypertension is a chronic elevation of blood pressure resulting from the obstruction of blood flow within the kidney (secondary hypertension) or without apparent cause (essential hypertension). One kidney disorder associated with secondary hypertension is pyelonephritis, the inflammation of the renal pelvis of the kidney as a result of bacterial infection, usually responsive to antibiotics. It has not been reported, however, that there is any correlation between essential hypertension and asymptomatic bacteriuria (bacteriuria observed in patients not reporting symptoms of urinary tract disorders). According to N. M. Kaplan, Clinical Hypertension, 14 (3d. ed. 1982), bacteriuria is found in 2-5% of hypertensives. Most of these positive cultures were of gram-negative rods. The method of the present invention has demonstrated a much higher incidence of bacteriuria in hypertensives, perhaps as high as 90%, and that cocci or "exploded cocci" are found in considerable numbers.

SUMMARY OF THE INVENTION

This invention utilizes a lipid wash to remove substances in urine which otherwise interfere with the retention of bacterial cells after aqueous staining. By virtue of the improved specimen preparation method herein contemplated, it has been demonstrated that certain diseases of hitherto unknown or uncertain eitology are associated with bacteriuria not detected by prior methods. Application of antibiotic therapy appropriate to the detected organisms may then offer therapeutic benefit.

Those illnesses most frequently benefited by the use of antibiotic therapy following detection of bacteriuria by the present invention as set forth in the following examples include: Rheumatoid Arthritis (and the related bursitis, tendonitis, tempero-mandibular arthritis, sacro-iliac arthritis, carpal-tunnel syndrome, temporal arteritis. paleandromic rheumatism), and "essential" hypertension.

Although a limited number of cases have been investigated, diagnosed and successfully treated by me, it is believed that the present invention can also be applied to the treatment of other diseases or conditions which include the following: rheumatic fever, systemic lupus erythematosis, scleroderma, classic migraine, transient ischemia, mitral valve prolapse, urinary tract stones, reversible reduction in renal function, "brittle" diabetes mellitus, lymphangitis manifest as chronic brawny swelling or bacterial elephantiasis, otherwise unexplained edema, proteinuria or fatigue, and many instances of diffuse backache.

The above disclosed technique for determining the presence of bacteria, especially cocci, in the urine—generally exceeding 20 cocci per square millimeter—is useful as a general diagnostic technique which should be utilized in the diagnosis of the above listed diseases or conditions. Once the cocci have been found, an effective amount of an antibiotic effective against the cocci is administered. Relatively massive doses of antibiotic are administered— while 600 mg per day of clindamycin is effective, an intravenous dose of 1 gram to 2.4 grams per day is preferred. (Those dosages may be adjusted for other routes of administration.)

Typically, when cocci have been found in urine, utilizing the method of this invention, antibiotic therapy has effectively eliminated the cocci and has alleviated the symptoms, signs, and often the abnormal laboratory findings of the patient. Small cocci have been found in patients suffering from rheumatic fever, systemic lupus erthematosis, migraine and other headaches, mitral valve prolapse, and renal failure. Treatment with antibiotics in each case has typically alleviated the symptoms, signs and often the abnormal laboratory findings of such patients.

One object of the invention is to detect bacteria in urine that might not be detected by standard methods.

Another object of the invention is to ensure that all bacteria in a urine sample are collected in the sediment to be analyzed by adequate centrifugation.

Another object of the invention is to ensure that the bacteria-containing sediment from a centrifuged urine sample is not in whole or in part washed away by any aqueous media employed in the preparation of the sample for examination. Another object of the invention is to alert the physician to the possibility that antibiotic therapy, specific to the organisms found in the urine by the novel preparation methods of this invention, might improve the patient's condition.

Another object of the invention is to provide therapeutic relief in cases of rheumatoid arthritis, essential hypertension, and other diseases or conditions found to be associated with significant bacteriuria.

Other objects will be apparent to a person of ordinary skill in the art after studying these specifications and claims.

DETAILED DESCRIPTION OF THE INVENTION

Preparation of the Urine Sample for Examination

The examination and preparation steps of the preferred embodiment are described below:

(1) Staining of Formed Structures: It is preferable to first add a vital stain (e.g. Brilliant Cresyl Blue) along with a chemical which gently fixes the structure of formed elements of urine (casts, leucocytes, tubular epithelial cells, etc.) as well as the bacteria (dead or alive). Such a chemical may be glutaraldehyde in dilute solution. Too much of a cross-linking chemical may gel any protein dissolved in the urine and prohibit further study. Although this step enhances the study of formed elements at 100 diameters magnification and it enhances the preparation of some bacteria, it is usually not essential.

(2) Centrifugation: In the ordinary practice urine is centrifuged at a Relative Centrifugal Force (RCF) about 1000 times gravity. Usually the RCF is not specified, is ambiguously stated, or is specified as so many revolutions per minute of a given centrifuge. Centrifugation of samples in the past has often been inadequate. Theoretically, a small particle may not sediment in any amount of time at too low a RCF (e.g. colloids). In practice, some bacteria will not sediment at the RCF of the "clinical centrifuge". Damaged bacteria may have a lower density approaching that of the urine, which itself varies in density from sample to sample. It is not infrequently important to apply a strong enough RCF to sediment all bacteria. Preferably, the urine is centrifuged at 4000 times gravity for 10-15 minutes. (This is as effective as 4500 times gravity for 30 minutes.) The tube may conveniently be conical, from 15 ml. to 50 ml. depending on the centrifuge.

(3) Dispersion: After decanting the supernate the sediment is dispersed in the remaining clear fluid (about (0.1 )ml. in an ordinary 15 ml. conical tube) and the suspension is spread on a clean glass slide. 4) Wet viewing: The sediment is viewed without a coverslip at 100–400 diameters magnification. (A coverslip may damage casts and other formed elements, and removal of the coverslip would be necessary to stain the slide.)

(5) Drying: The slide is then dried slowly, e.g., under the airstream of a low powered hair dryer.

(6) Removal of Lipids: The lipids which I have found in urine are in the range of polarity of the phospholipids. Preferably, they are washed off by a mixture of pure methanol and halogenated hydrocarbon (e.g., 1,1,1-trichlorethane) at 50:1.

(7) Further Fixation: Results may be improved by further fixation at this point. Although dilute glutaraldehyde in methanol is useful, if it is followed by a solution of copper phthalocyanine in methanol, the structures of cells and of damaged bacteria are better preserved.

(8) Washing: preferably the slide is washed with pure methanol to remove residual copper phthalocyanine.

(9) Staining: A conventional non-fluorescent stain, such as the Gram stain, may be used, as may a counterstain such as safranin. The slide is dried and examined at 1000 diameters without a coverslip.

Should the urine contain significant quantities of glucose (e.g., the urine of a diabetic out of control, perhaps as a result of a urinary tract infection) then the glucose (in the interstices between particles of sediment) will dry on the slide, will not be fixed by the glutaraldehyde (GTL) or by the copper phthalocyanine (CuP) in methanol, will redissolve in the aqueous stains, and will release the sediment from the slide. Similarly, when the urine contains 30 mg% or more of soluble protein (albumin, etc.), that soluble protein will interfere. Unlike glucose, that protein will be fixed by the GTL and CuP and will form a brittle film on the slide. Large portions of this film may break off in the staining procedure. Even then there is a remarkable tendency for the released film to leave behind the formed elements (especially the bacteria) which remain fixed to the slide. That portion of the homogeneous film of protein which remains on the slide stains much like the formed elements, and during the examination for bacteria using the oil objective (1000 x), the stained protein film may obscure bacteria and important formed elements in the sediment (wbc, rbc, tubular epithelial cells, and casts). Since the bacteria are usually demonstrable either inside the protein or in the areas of the slide free of protein film, the preparation is not lost. In addition to the urines containing excessive amounts of glucose and of protein, a few urines contain other soluble non-lipid material (perhaps phosphates) which does not fix to the slide and which releases the sediment from the slide. All of these urines are better studied after washing the sediment. Often there is enough sediment remaining in the test tube used in the initial centrifuging to proceed with a wash.

Thus, in a modification of the method, in place of Step 3 above the sediment is washed with a solution agent, preferably ionic in nature, such as 0.2 molar NaCl, preferably rendered slightly hypertonic to plasma, and passed through a 0.22 micron filter to render it bacteriologically sterile and particle free. It is preferable to add a small quantity of fixative to this wash solution, e.g. 0.5 ml of the methanolic CuP fixative and 5 ml glacial acetic acid to 1 liter of the 0.2 M NaCl. If a blue sediment appears with standing, it can be filtered or decanted. The packed sediment of the fresh urine (of the usual preparation above) is dispersed in about 3 ml of wash solution and centrifuged, e.g. 4000 g for 5 minutes. The supernatant solution is decanted and the sediment is washed with another 3 ml. The twice washed sediment is spread on a slide where under low magnification (100 x) formed elements (casts, wbc, rbc, tubular epithelial cells, bacteria) are more readily seen than in the unwashed sediment. When dried on the slide the washed sediment adheres very well to the glass through fixation and staining. The gross appearance of Gram-stained slide is different (see photo - more dense, and red instead of blue) because some material (presumably glycoprotein) which stains blue with the copper phthalocyanine has been removed. However, the Gram stain is not altered. Gram positive bacteria still take the positive stain. But having removed most of the protein and glucose, Gram negative sediment (bacteria, cells, casts), previously obscured by the similar homogeneous stain of precipitated soluble protein, now stands out.

Since a heavy deposit of copper phthalocyanine will absorb ultraviolet light, this fixative cannot be used for UV fluorescence staining. Step #7 may be modified to permit UV fluorescence staining by either increasing the glutaraldehyde concentration or the duration of exposure to the fixative. Then the slide may be stained with the UV flourescing stain, e.g., a stabilized solution of acridine orange as illustrated in the figures to follow. Acridine orange, and most similar cationic dyes, themselves exert a fixative effect, and so use of the UV flourescing stain may in some instances be substituted for use of a fixative.

In a further modification of this novel method of specimen preparation, insoluble proteins are removed by bacterial or fungal proteases, or proteolytic enzymes of animal origin such as crystalline trypsin and chymotrypsin. The enzyme may be used after fixation of the sediment to the slide, but it is preferable to use it before the wash.

A slide prepared in any of the above procedures may be treated with a proteolytic enzyme after fixation with GTL, but preferably before fixation with CuP. A solution of enzyme in saline is simply applied to the slide. The slide is incubated at room temperature or at 37 degrees C., washed with saline, fixed again and stained.

It is preferable to treat the sediment with enzyme in the test tube before the fixative is added. Fresh urine is centrifuged at 4000 x G for 10–15 minutes without fixative or preservative. The supernate is decanted and crystalline trypsin (or a strong solution of bacterial protease) is added to the sediment. After stirring the tube is incubated (preferably at 37 degrees C) for 10 minutes and then centrifuged at 4000 x G for 5 minutes. The drop of new supernate is drained off, and the sediment is washed twice as above.

This treatment removes some of the insoluble proteins. Two advantages are noted. First, some of the sediment is removed but bacteria and even degenerate bacteria, cells, and casts are spared. This provides a means to concentrate important sediment such as bacteria. Second, the staining of some bacteria is changed. Most notable is the emergence of Gram positive cocci in sediments that contained only Gram negative cocci in their unwashed or washed preparations. Since the Gram positive material is peculiar to the cell wall of these bacteria, it is quite unlikely that each of two proteolytic enzymes would create the conditions for a positive stain (retention of the iodinated crystal violet). Instead it is quite likely that each proteolytic enzyme removed a protein, for example a human antibody adhering to the bacterial cell wall, that prevented the Gram positive dye from penetrating or fixing to the cell wall.

In still other embodiments, the urine sediment is treated with other enzymes, or antibodies to reveal additional information. relating to the identification of bacteria or bacterial fragments in the sediment. Among the enzymes that may be so employed are amylase (to remove carbohydrate polymers), DNases, RNases, lipases, lechithinases, sphingomyelinases, sialases, neuraminidases, and hyaluronidases. Among the dyes which may be employed is acridine orange, which may be used to demonstrate nucleic acids by fluorescence. Among the antibodies which may be utilized are tagged (e.g., fluorescent) anti-human IgG, polyclonal or monoclonal, to demonstrate the presence of the human IgG on the bacteria of the sediment.

Other positive embodiments of this procedure, not differing in essence from the invention herein disclosed, will be apparent to a person of ordinary skill in the art.

Observations of Bacteriuria

By the method of the present invention, small cocci have been consistently found in the urine of patients with various forms of rheumatoid arthritis, systemic lupus erythematosis, and rheumatic fever and, in those instances examined, patients with migraine, bursitis, tendonitis, temporal arteritis, and diffuse persistent backache. It appears that a large array of seemingly unrelated illnesses may, by this approach, become reclassified as illnesses which are related to the appearance of small cocci in the urine, and that, from the beneficial effects of antibacterial treatment, such a reclassification may be meaningful. The actual diverse illnesses mentioned above may simply be responses to the same bacterial invasion or to similar bacterial invasions and the diversity) or different illnesses) may simply be varied responses by the human host to a given invasion.

Moreover, this novel preparation procedure has been used to detect the association of larger or damaged ("exploded") cocci in the urine of patients suffering from hypertension, transient ischemia attacks, and in the few cases seen, mitral valve prolapse and IgA nephropathy. Again these seemingly unrelated illnesses may simply be various responses to the invasion by said bacteria. Indeed most of these illnesses have in common an early lesion in the tiny arteries in the organs involved.

Treatment of Rheumatoid Arthritis

Numerous cases of Rheumatoid Arthritis (RA) examined by applicant have also had large numbers of small coccus in their urine. Applicant has reviewed 26 cases of RA seen in the past few years. Each had small cocci in the urine in great numbers, often hundreds of cocci per 1,000 x, oil immersion field, (See FIG. 2), and each has had significant improvement of the illness on antibacterial therapy without any other change in medication. Some have even had a full remission of the illness with eradication of the bacteriuria.

Among the more useful therapeutic agents the antibiotics lincomycin and clindamycin, alone or with a aminoglycoside antibiotic, seem to be the most useful. Other useful therapeutic agents are cephalexin, cephradine, cefazolin, cephalothin, novobiocin, and some of the penicillins. More antibacterial agents may also be found to be useful, and the methodology described herein is valuable to determine whether the agent is effective in vivo. These antibiotics are best given parenterally, largely to increase the dosage. When the drugs are given parenterally the dosage can be controlled and the response has been predictable. With clindamycin or lincomycin about 600 to 900 mg. per day can be given by mouth. Better and more predictable results are had by administration of 1.2 to 2.4 gm. per day of either drug by way of a continuous intravenous drip. The drug dosage is continued at least until the urine sediment, examined as disclosed above, no longer shows the presence of cocci.

Other useful drugs for the treatment of RA include cephazolin administered intravenously at a level of at least 1000 mg. per day up to 8000 mg. per day; cefamandole given either I.M. or I.V. at 1000 to 3000 Mg. per day; cephradine given at 1000 mg. per day by mouth, cephalexin at 1000 to 2000 mg. per day by mouth; cephalothin given at 2000 to 8000 mg. per day by vein; moxalactam given at 2000 to 12000 per day by vein; and novobiocin at 1000 to 2000 mg. per day.

A few examples follow:

1) Mrs. J. N. F. is a 58 yr. old housewife. In 1972 she began having arthritis in her left knee, right foot, and right hand, and then bursitis in the left shoulder. She received non-steriodal anti-arthritic medications with limited success. In 1980 an orthopedic surgeon injected a corticoid into her right elbow with good relief. In December 1980 she first noticed a rheumatoid nodule at the base of her left index finger. When seen in February 1981 she also had a trace of edema of both legs. Her stained urinary sediment contained large numbers of encapsulated diplococci. On oral cephalexin (at a dosage of 1 gram per day) and ibuprofen she realized major relief in a week. The cephalexin was continued. In two months the rheumatoid nodule began to shrink and it disappeared several months later. At 3 months she only required 400 mg. of ibuprofen a day to control her arthralgia. That month the diplococci reappeared and she had a mild flare-up of her arthralgia. Both the bacteriuria and the flare-up responded to 5 days of clindamycin and then cephalexin was resumed. Since then and to date she has had only a few mild flare-ups, each associated with a bacteriological relapse and each responding to a change in the antibiotic, usually to clindamycin, followed by resumption of cephalexin.

(2) Mrs. G. C. was a 47 year old housewife with 22 years of severe RA when first seen by me and hospitalized in 1981 for antibacterial therapy. She had had virtually every known therapy including courses of gold, penicillamine, immunosupressants, 60 mg./day of prednisone, non-steroidal antirheumatics, and acupuncture in a London clinic. She had had 15 operations to replace 10 joints and two more joint replacements had been recommended in a nearby clinic. She was in constant pain. Her urine contained large numbers of small streptococci. The urine culture was negative. Hemoglobin 11.6 g/dl. wbc 11,900/cmm, RM factor negative, and ANA only +1 undiluted. Complement C3 and C4 were normal and the IgG was slightly low. She was given 1.8 g. of clindamycin and 1 g of cefamandole daily by a continuous I.V. drip and maintained on the prior medications. In 1 week she was asymptomatic and discharged on the same medications plus clindamycin. After she began to walk she fell and fractured her hip. The hip was replaced elsewhere. About 5 months later she had a bacterial relapse followed by a clinical relapse. Again she had good relief, but she continued to relapse until one day she fell, sustained a shoulder fracture and was hospitalized elsewhere.

(3) S. McC. was a 24 year old staff nurse who had fatigued easily for several years, had recurrent back pain primarily in the sacroiliac area, and had episodes of epigastric pain with nausea and persistent vomiting. She had been followed by subspecialists in medicine since she was a nursing student and she had been hospitalized by a gastroenterologist because of the same trouble. No diagnosis had been established. Non-steroidal antiarthritic medicines offered minimal benefit. A catheterized urine showed small cocci and a culture grew out between 6,000 and 50,000 colonies of a diphtheroid that was sensitive to multiple antibiotics (Microorganisms can become distorted in a hostile environment such as urine, but I believe that the organisms photographed under the microscope are more likely to be streptococci than diphtheroids). In a continuous I.V. drip she received 1.2 g clindamycin and 1 g cefazolin per day for one week. All symptoms disappeared except the pain of sacroiliac arthritis. That was relieved by intra-articular injection of a corticosteroid. Soon after discharge she lost 9 lbs. of edema, regained her stamina, and began working 16 hour shifts. The abdominal symptoms have never returned. She has had one mild relapse of malaise preceded by a bacterial relapse. Her urine often contains gram negative rods which give her only mild bladder symptoms. One relapse of sacroiliac arthritis required another I.A. injection of steroids. She is well and she takes no anti-arthritic medication.

(4) C. LaF. is a 50 year old housewife with 7 years of Progressive painful RA in multiple joints, progressive deformity of her hands and swelling of her knees. She had been treated by many physicians including two rheumatologists, and she had received virtually every modality of therapy, including gold, penicillamine, methotrexate, plaquenil, steroids, etc. She had been gastroscoped for sequellae of non-steroidal antirheumatics. She had become depressed and suicidal. Since her first pregnancy 26 years before she had used diuretics for swelling of her legs. She got up to urinate 3-4 times a night. Admission urine examined according to the present method showed small encapsulated diplococci which are probably streptococci. The corresponding hospital urine culture show(R)d no growth. Her RA titer was 1:160, ANA 1:2500, and sedimentation rate 110/hr. She had inflamed metacarpo-phalangeal (MP) joints of her hands (knuckles), there was ulnar deviation of the fingers typical of the disease, the knees were swollen and there was a large rheumatoid nodule beneath the left great toe. She was given 2.4 gm of clindamycin with 1 gm of nafcillin by vein per day and miantained on her previous medication which included 10 mg. per day of prednisone. On the third day her urine contained no bacteria and she was free of pain. On the 10th day she was discharged on 600 mg. of clindamycin and 10 mg. of prednisone a day. After 2 weeks she had a recurrence of the Gram positive dipplococci along with casts in her urine, and this was followed by a minor relapse of her arthritis. Cephalexin and tetracycline failed to influence either the urine findings or the clinical course and 1 week later she had 100 mg.% Proteinuria. She was given tobramycin and lincomycin I.M. and clindamycin and 600 mg./day of aspirin by mouth for a week with a brief bacteriological remission and brief clinical improvement. Ampicillin with dicloxacillin (2 penicillins) were without effect. Clindamycin at 600 mg/day by mouth for a month resulted in some improvement but she again relapsed. Cloaxacillin (penicillin) and then nitrofuradantin did not affect either the urine sediment or the symptoms. She was bothered by sinusitis. Four months after hospitalization she was again started on 1.2 gm of clindamycin by mouth with disappearance of the cocci from the urine and significant clinical improvement. Off clindamycin she again had a bacteriological and a clinical relapse. There may have been some improvement on Bactrim (sulfasoxazole with trimethoprim), but in 2 weeks she again required hospitalization.

In December 1981, she was hospitalized and given 1.8 gm of clindamycin I.V. for 1 week, again with complete relief of pain and swelling. Her RA assay, previously positive 1:160, had become negative, and her ANA was still normal. She was discharged on cephradine. One month later her clinical improvement continued and the rheumatoid nodule became much smaller and softer, but she had a bacteriological relapse. Clindamycin at 600 mg/day was ineffective and she was hospitalized again in January 1982. Her RA was positive 1:10 and her erythrocyte sedimentation rate was 41 mm/hour. She had a bacteriological and clinical remission on 1.2 gm/day of clindamycin I.V., and she was discharged on 900 mg/day of clindamycin by mouth.

In March 1983, following mild sinusitis and in spite of oral clindamycin at 600 mg/day she again required hospitalization. Her RA was now positive in a dilution of 12560, and her erythrocyte sedimentation rate was 110 mm/hour. The ANA remained negative. Again on clindamycin at 1.2 gm/day by vein she felt better in 48 hours and she had a clinical and bacteriological remission. She was given 100 mg/day of azathioprin in the hope of reducing the auto-immune response. One day after discharge she noted swelling of her left leg and dicoumarol was begun. The leg problem subsided. Two months later, in spite of oral clindamycin at 600 mg/day and cephradine at 1 gm/day she again required hospitalization following 1 week of a flu-like illness. Her joints swelled and 10 ml. of bloody fluid was removed from her right knee. The joint fluid was devoid of bacteria by stain and by culture. She had a wbc of 18,000, but her RA was positive only to a dilution of 1:20 and the ANA remained negative. She had developed diabetes mellitus and required insulin for the next 2 months only. Again she was given intense antibiotics including 1.2 gm/day of clindamycin. She was discharged on 600 mg/day of clindamycin by mouth and she has not been hospitalized since.

In September 1983, she began to relapse again, and by October she was in severe pain. Under the belief that the streptococcus seen in her urine before each flare-up of arthritis (and since isolated from her urine) was indeed the antigen that provoked the auto-antibodies that caused inflammation of her joints, it was postulated that some component of that streptococcus provoked an antibody that cross-reacted with her joint tissue. If that component were within the streptococcus, the destruction of the streptococcus would liberate slowly in the natural disease, but massive clindamycin or lincomycin would liberate a large dose of antigen which would act like a booster shot. Thus, instead of repeated hospitalizations (which she began to refuse), an attempt was made to give her a large dose of lincomycin (to destroy the streptococcus) along with a large dose of cyclophosphamide to eliminate the "booster" effect. In August 1983, she was given her first I.V. of 1.2 gm lincomycin with 0.5 gm cyclophophamine. Except for 2 doses of 1.0 gm of cyclophamide this was repeated at weekly intervals for 5 weeks. This dosage was then continued at increasing intervals to a total of 9 sessions of IV. therapy with 7.5. gm of cyclophosphamide. She takes 600 mg/day of clindamycin by mouth also. She has been free of symptoms since the onset of this treatment and her urine has been free of streptococci.

In summary; a 50 year old housewife with very severe, rapidly progressing arthritis had 6 remissions on brief courses of 1.2 to 2.4 gm/day of clindamycin by vein in the hospital, but relapsed on oral clindamycin and on other antibiotics. Finally she had been in a prolonged remission using I.V. lincomycin with cyclophosphamide at increasing intervals. Diabetes mellitus appeared briefly in the period before cyclophosphamide, but her blood sugar returned to normal without insulin in 2 months.

(5) P.M.G. is a 23 year old niece of C. LaF.. (#4 above). Five months before I saw her she had an attack of sinusitis followed by headaches, chills with fever and then increasing polyarthralgia. She had no joint deformity, but she feared the progressive disease suffered by her aunt so much that she delayed her wedding. She had no nocturia and no other symptom attributable to the urinary tract. Physical examination revealed only normal findings except for rhinitis and tenderness in her finger joints. Her urine showed diplococci and "exploded" cocci. On clindamycin at a dosage of 600 mg/day by mouth and no antiarthritic drug, she had rapid relief of her pain, chills, and fever. Four months later she showed larger cocci in her urine but had no symptoms. At 7 months she had sinusitis, a right sided headache, the reappearance of cocci in her urine and temperomandibular arthralgia. She quickly became asymptomatic on a sequence of antibacterial agents. After almost a year with no recurrence she was married.

(6) S.S.B. is a 32 year old woman who had had surgery for partial obstruction of the right ureteropelvic junction at age 12. For the next many years she had recurrent "bladder infections". At 24 she began to have periods of headaches, malaise, weakness, arthralgia, and leucopenia. Sometimes she also had tiny sterile abscesses in her skin, even in the thick palmar skin. On each of these occasions her urine contained large numbers of tiny cocci which failed to grow in culture. The organisms are stained by a fluorescent dye which glows yellow to orange when bound to nucleic acids. The pattern of nucleic acids clearly outlines the small cocci. Her ANA titer rose to 1:80. The RA test remains negative. A radioisotope "triple renal scan" was normal. Each of the episodes quickly responded to intravenous lincomycin or clindamycin at a dosage level of 1.8 to 2.1 g/day with cefazolin.

(7) T.K. is a 28 year old lawyer. Three years ago he complained of 3 months of progressive pain and swelling in the joints of his hands and in his previously injured knee. The onset was insidious and without warning. He had no other symptoms. The diagnosis elsewhere was RA. His urine contained cocci. On clindamycin and ibuprofen he had a remission in one week, but his urine continued to show "exploded" cocci. This finding cleared following a single initial injection of 0.6 grams of lincomycin and 600 m/g day of clindamycin administered orally for 6 days. He was maintained on tetracyline for 4 months and he has been asymptomatic since.

(8) E. J. R. H. is a 59 year old retired salesman with two years of progressive arthritis beginning in his left shoulder and within a few months continuing in almost every joint in his body including the temperomandibular joints, hips, knees, shoulders, elbows, wrists, and fingers. He also had a 1 year history of bilateral kidney stones. He had received iron shots and vitamins for his anemia. When he arrived he was taking naproxen and 10 mg. prednisone a day without relief of the pain or swelling. Physical examination revealed evidence of arthritis of all of the above joints. I found streptococci in his urine, but the hospital laboratory reported no growth in the urine culture. He was mildly anemic with a hemoglobin of 11.2 gm. %. His erythrocyte sedimentation rate was 101 mm./hour. The C reactive protein was positive. The RA was positive to a titer of 1:10,240 and the ANA to a titer of 1:5,120. The serum albumen was low at 2.5%. The IgM was elevated at 503 mg. % (75-125), IgA at 398 mg. % (150-250), and IgE at 490 u/ml (less than 122). The complement C-3 was normal, the C-4 marginally low, and the CH-50 was low at 30 $\mu$ (60-120). Pyelograms showed an atrophic left kidney and right renal stones. He was given 1.8 gm clindamycin and 1.0 gm cefazolin per day by vein and 160 mg tobramycin I.M. for 5 days. Prednisone was continued at 10 mg per day and the NSAID was continued. A rapid remission of arthritis began within 24 hours and within 3 days he was symptom free. His appetite and energy returned. On the 6th day renal stones were surgically removed. Recovery was uneventful.

At 2 months he had some swelling of several joints on awakening. The swelling would subside by mid-morning. His urine showed cocci and he was given clindamycin 600 mg/day for 7 days. At 4 months he had residual shoulder pain. He had regained 6 pounds and his color was better. He was again given clindamycin. He passed another renal stone. At 7 months and at 9 months he was without symptoms. He was still slightly anemic at 7 months.

(9) C. S.: When first seen C. S. was a 39 year old housewife-college professor who began having arthritis in the proximal interphalangeal joints, hips, knees, and back about 4 years before I first saw her. She complained of nocturia, a few times a night for several years.

In January and in July of 1979 she was admitted to a hospital in Alexandria, Va., complaining of severe low back pain radiating to thighs and to abdomen. It was aggravated by extension of her back but by no other motion. She gave a past history of recurrent urinary tract infections. On the second admission she had mononucleosis also. No lab test was done for RA except for a bone scan which was negative. Her back pain was attributed to extensive ballet lessons. Because of the X-ray changes in the spine the discharge diagnosis was Degenerative Arthritis. She was given naproxen, a nonsteroidal anti-arthritic.

In April 1981, she was hospitalized in Oberlin, Ohio, where she was diagnosed clinically as having "chondritis" in chest and she was given naproxen again. Her ANA, ASO, and C reactive protein were normal. Upper GI X-rays, gastroscopy, barium enema, EKG, etc. also normal.

On physical examination she was found to have fusiform swelling of her fingers due to inflammation of the p.i.p. joints.

Her urine showed a few dipplococci and +++ "exploded" cocci. A course of cephalexin was without benefit. A few Gram negative rods appeared in her urine and a course of ampicillin and cinoxacin eliminated the rods, but the cocci remained and the arthritis got worse. Septra (trimethoprim with sulfasoxazole) was without benefit, and tetracycline caused nausea. Seven months after I first saw her she had acute sacroiliac arthritis, and the normal curvature of her lumbar spine had reversed. The cocci persisted in her urine on microscopic examination.

She was admitted to the Touro Infirmary in New Orleans where a urine culture was negative, her white blood count was low at 3,400, and her ANA was positive to a titer of 1:80. Complement C-3 and C-4 levels were both reduced. Other tests bearing on RA were negative. X-rays of the spine showed only degenerative changes. She was given 1.8 gm./day of clindamycin I.V. for 3 days and then 600 mg./day by mouth, and she was also given 160 mg./day of tobramycin for 5 days. By the fifth day she had become free of all symptoms and she was discharged on oral clindamycin, 600 mg./day. When seen 1 month later she was still on clindamycin and she was doing well. Three months later she returned in a relapse. She had discontinued the antibacterial agent and had begun prednisone at 20 mg./day. Her fingers were again swollen and her back trouble had returned. Her urine contained 30 mg % protein, cellular casts, and cocci. She was again hospitalized.

Her admission urine culture was reported as showing no growth. Her white blood count was low at 2,700 and rose to 4,800. She was anemic with a Hct as low as 31.6%. The ANA was again positive at 1:80, the complement C-3 and C-4 were both low again. The IgG was low and the IgM was slightly high. All other tests for RA were negative again. She was given a continuous I.V. drip containing 1.8 gm. of clindamycin and 1.0 gm. of cefamandole a day, and she was given 160 mg./day of tobramycin. On the fifth day she was discharged completely symptomatic. Discharge medications were prednisone reduced to 15 mg./day, naproxen and 600 mg./day of clindamycin.

Two followup urines were devoid of cocci. She went to another city where she and her husband took faculty positions. Six months later she wrote that she had a relapse.

TREATMENT OF ESSENTIAL HYPERTENSION

Most cases of essential hypertension have been found to exhibit significant numbers of cocci in the urine. The cocci in this disorder are usually different than those in the rheumatoid illnesses in that they are larger and there is often a preponderance of forms that resemble the photographs in the literature of cocci that have exploded after exposure to some antibiotic or to some immune mechanism. For convenience these forms are referred to as exploded cocci. They may be different species, such as staphylococci instead of streptococci. That these microorganisms are in the chain of causation of the hypertension is demonstrated by ridding the patient of the cocci by antibiotic treatment and observing the patient's improvement either in terms of lessening the need for antihypertensive drugs or eliminating the need of antihypertensive drugs. The preferred drug dosage levels are the same as above described with respect to RA.

(1) Dr. W. S. is a psychiatrist. At age 30 he had a period of hypertension that went away. At age 57 he noted increasing fatigue in his daily jogging in the park. His wife, a nurse, found his B.P. to be 190/140. He began 50 mg of chlorthalidone a day and increased it to 100 mg a day with some drop in his pressure but he became weak. On examination his B.P. was 150/100. He was overweight and his retinal arterioles were slightly narrowed. X-ray of the chest was normal. An EKG showed low T waves. The serum sodium was 131 meq/l and the potassium 4.1. The urine showed hyaline casts, gram positive and negative cocci, and exploded cocci. Chlorthalidone was administered at a dosage of 100 mg/day for 3 days and clindamycin at a dosage of 600 mg/day for 7 days was added. Three days later his B.P. was 118/80. Ventricular premature beats cleared on an oral potassium supplement. At 1 week he was given cephalexin at a dosage of 1 gm/day for 7 days because a few cocci remained in the urine. At 3 weeks he became weak with a B.P. of 110/70. Chlorthalidone was reduced to 50 mg per day and quinidine was given for recurrence of his ventricular premature beats. A trace of proteinuria temporarily increased to 30 mg. % proteinuria. Trimethoprim at a dosage of 200 mg/day was substituted for cephalexin because of continued exploded cocci. At 6 weeks he was clinically well with a B.P. 110/74. Proteinuria was reduced to normal and a few cocci remained. Chlorthalidone was reduced to 25 mg per day and cephalexin was restarted. At 3 months he was well, his B.P. was 110/74, his urine was free of bacteria, and he took 25 mg chlorthalidone only at his whim.

(2) C. H. is a 35 year old drug representative. In November 1982 without symptoms he discovered that his B.P. was 165/120. Repeat determinations were similar. On 2 mg per day of prazosin his blood pressure fell to 130/78 but he fatigued more easily and in slow jogging his pulse rate rose to 105 per minute. At rest his pulse rate was high. Physical examination revealed only normal findings. His urine contained only a trace of protein. The sediment contained no formed elements, but it showed ++ encapsulated cocci and ++ exploded cocci. Prazosin was stopped and he was given cephalexin at a dosage of 1.5 gm/day. Eight days later only a few cocci remained. *In two weeks his blood pressure was normal and it has remained so to date.* At 3 weeks he had 30 mg. % proteinuria and +++ exploded cocci. On 600 mg/day of clindamycin and other cephalosporins for 7 days the proteinuria stopped, but he still shows cocci in the urine on occasion. After 2 or 3 months of antibiotic therapy he noted a return of his sense of well being and stamina, his resting pulse rate is 56 to 60, and jogging does not cause a tachycardia.

(3) T. M. is an obese 58 year old salesman. In 1966 in a routine physical examination at work he was found to have a B.P. of 240/120. His only symptom was nocturia. On antihypertensive medicines he began to have headaches and visual difficulty. When I first saw him seven months later his B.P. was 240/160, he had flame-shaped retinal hemorrhages, 300 mg. % proteinuria, mild azotemia, and innumerable small cocci in the sediment. On 75 mg./day of hydrodiuril the pressure fell to 190/110 but the symptoms persisted. Intramuscular nafcillin caused a spell of weakness with a blood pressure of 160/90 (perhaps this was a Herxheimer reaction because he was not and is not allergic to nafcillin or any other penicillin). After 3 weeks on 1 gram per day of novobiocin he was asymptomatic with a B.P. 130/70, with 750 mg. of methyldopa and 75 mg. of hydrodiuril a day. After 5 weeks of therapy his retinal hemorrages had stopped and the retinal arterioles appeared normal. At 2 months his blood had fallen to 100/66. His methyldopa was reduced to 500 Mg./d and hydrodiuril to 50 mg./d. Cloxacillin was continued. At 6 months the B.P. was 110/70 and hydrodiuril was reduce to 25 mg./d. At 2 years he was off all hypertensive therapy and his blood pressure remained in the range of 120/80 to 140/90. To date he has had no restriction of dietary sodium. Two and one half years after first seen he had staphylococci in his urine and his blood pressure rose to 150/100. On resuming a dosage of 1 gram per day of a staph-specific penicillin it fell to 130/80. Six years after first seen he had become obese and he again had staphylococci in the urine. It was necessary to resume antihypertensive therapy for several months. At 11 years he developed diabetes. At 12 years exploded cocci reappeared and have since been difficult to eliminate. He had a myocardial infarction with persistent angina. Since that time he has to take as much as 750 mg. of methyldopa and 50 mg. of hydrodiuril a day. He developed gout, but he has not changed his eating habits. In April 1983 (16 years) his blood pressure was 140/80, height 5 feet 6 inches, weight 197 lbs., and he was taking allopurinol, antiangina drugs, penicillin, and the same doses of above drugs for hypertension. In summary T. M. had a prolonged remission on antibiotic therapy alone and now, 16 years after malignant hypertension, he is still on low doses on antihypertensives.

(4) W. R. is a 67 year old retired college professor who had had back pain intermittently since his college days. He consulted me because of 1 month of pain in his ankles followed by pain and swelling of his knees which prohibited him from gardening. He was taking 20 mg./day of piroxicam with minimal relief of pain. He had had hypertension for 20 years controlled to 160/90–95 by 2 mg. of prazosin and 50 mg. of atenolol daily. On examination his B.P. was 220/110 but it fell with rest to 140/80. The only other abnormal finding was a swelling of the left knee. His urine showed a few tubular epithelial cells and only a few encapsulated diplococci. Prazosin was stopped and clindamycin at a dosage of 600 mg/day for 7 days was started. After 1 week he felt better and his B.P. was 136/72. His urine showed an occasional diplococcus and +++ exploded cocci. On 1 gram/day for 10 days of cephalexin the B.P. fell to 112/66 and his atenolol was reduced to 25 mg./day. At 4 months he was off all antihypertensive medicines and his blood pressure rose to 160/90. Antihypertensives were resumed for only 1 month. When discontinued the B.P. remained normal. When seen this month his blood pressure was 140/80. He stated that he felt better than he had in many years and that he had given up wine which he had drunk only to feel better. He lost 7 lbs. Now he has no arthralgia or joint swelling, but he elects to continue the piroxicam. He is concerned only that his potency has not returned.

(5) J. S. G. is a tense, overweight businessman with hyperlipemia who was taking 10 mg. of bendroflumethiazide daily when I first attended him 4 years ago. Physical examination and EKG were normal, but his urine contained a trace of protein and staphylococci, both free and in casts. On 1.5 gr/day of oral cephalexin and no thiazide his B.P. fell to 120/78. He has been on cephalexin at a dosage of 1 gram per day almost continually since, because he feels better on the drug. He has had 2 attacks of true vertigo which responded to thiazides and ammonium chloride. Alternate antibiotics were given for the associated upper respiratory infection. His B.P. has only once risen above normal and then briefly. All chemical screening is normal except for the lipids. He remains very active and does not follow any diet.

The enumeration of specific diseases above should not be taken to limit the value of the disclosed method in a clinical context as a guide to when antibiotic therapy may be appropriate.

I claim:

1. An improved method for direct microscopic detection of bacteria or bacterial fragments in a urine sample including staining the bacteria or bacterial fragments with an aqueous soluble dye, and microscopically observing the bacteria, in which the improvement comprises removing any lipid components of the sample prior to staining.

2. A method of treating rheumatoid arthritis in a human, comprising:
   (a) administering a therapeutically effective amount of an antibiotic effective against bacteria identified by collecting a sample of urine from a human suffering from rheumatoid arthritis and detecting any abnormal bacteria or bacterial fragments in the sample according to the method of claim 1; and
   (b) monitoring the urine for the presence of bacteria or bacterial fragments according to the method of claim 1 to determine efficacy of the treatment.

3. The method of claim 2, wherein the antibiotic is selected from the group consisting of clindamycin, lincomycin, cefazolin, cefamandole, cephradine, cephalexin, cephalothin, moxalactam, and novobiocin, and is administered according to the table below:

| DRUG | ROUTE OF ADMINISTRATION | DOSAGE MG/DAY |
|---|---|---|
| clindamycin | oral | 600–900 |
| | intravenous | 1200–2400 |
| lincomycin | oral | 600–900 |
| | intravenous | 1200–2400 |
| cefazolin | intravenous | 1000–8000 |
| cafamandole | intramuscular | 1000–3000 |
| | intravenous | 1000–3000 |
| cepharadine | oral | 1000 |
| cephalexin | oral | 1000–2000 |
| cephalothin | intravenous | 2000–8000 |
| moxalactam | intravenous | 2000–12000 |
| novobiocin | intravenous | 1000–2000 |

4. A method of treating essential hypertension in a human, comprising:
   (a) administering a therapeutically effective amount of an antibotic effective against bacteria identified by collecting a sample of urine from a human suffering from essential hypertension and detecting any abnormal bacteria or bacterial fragments in the sample according to the method of claim 1; and
   (b) monitoring the urine for the presence of bacteria or bacterial fragments according to the methods of claim 1 to determine efficacy of treatment.

5. A method of treating the following conditions: bursitis, tendonitis, tempero-mandibular arthritis, sacroiliac arthritis, carpal-tunnel syndrome, temporal arteritis, palindromic rheumatism, rheumatic fever, systemic lupus erythematosis, scleroderma, classic migraine, mitral value prolapse, urinary tract stones, brittle diabetes melitus, lymphangitis manifest as chronic brawny swelling or bacterial elephantiasis and proteinuria, comprising administering a therapeutically effective amount of an antibiotic effective against bacteria identified in a sample or urine according to the method of claim 1.

6. An improved method for direct microscopic detection of bacteria or bacterial fragments in a urine sample including the steps of staining the bacteria or bacterial fragments with an aqueous soluble dye and microscopically observing the bacteria, in which the improvement comprises centrifuging the sample at about 3500–4000 times gravity to sediment bacteria or bacterial fragments in the sample and removing any lipid components from the sediment prior to staining.

7. The method according to claim 6, in which the lipid soluble components are removed by use of a lipid solvent composition.

8. The method according to claim 6, in which the lipid solvent composition is a mixture of methanol and halogenated hydrocarbon.

9. The method according to claim 8, wherein the lipid solvent composition is mixture of methanol and 1,1,1-trichloroethane.

10. The method of claim 6, further comprising contacting the sediment with a tagged anti-human IgG antibody to demonstrate the presence of human IgG on the bacteria of the sediment.

11. The method of claim 7, wherein the antibody is tagged with a fluorescent dye.

12. The method of claim 6, wherein the sediment is contacted with acridine orange to demonstrate nucleic acids by fluorescence.

13. The method of claim 6, further comprising contacting the sediment with a proteolytic enzyme to aid in identifying any bacteria in the sediment.

14. The method of claim 13, wherein the proteolytic enzyme is selected from the group consisting of bacterial and fungal proteases, crystalline trypsin and chymotrypsin.

15. The method of claim 13, wherein the enzyme is selected from the group consisting of amylases, DNAases, RNAases, lipases, lecithanases, sialases, neumamidases, hylaronidases and spingomylelinases.

16. A method of detecting bacteria or bacterial fragments in a urine sample, comprising:
   (a) centrifuging the sample at a relative centrifugal force of about 3500–4000 times gravity to sediment bacteria and bacterial fragments;
   (b) separating the sediment from the supernatant;
   (c) spreading the sediment on a surface;
   (d) washing the sediment on the surface with a lipid solvent composition to remove any lipid components of the sediment preparatory to staining;
   (e) staining the washed sediment; and
   (f) microscopically observing the washed and stained sediment.

17. A method of diagnosing and treating rheumatoid arthritis or essential hypertension in a human comprising:
   (a) obtaining a urine sample from the human;
   (b) preparing the urine sample for microscopic examination by centrifuging the sample at about 3500 to about 4500 times gravity, separating the sediment from the supernatant, spreading the sediment on a surface, washing the sediment with a lipid solvent to remove any lipid components of the sediment, and staining the washed sediment;
   (c) microscopically detecting and identifying any bacteria or bacterial fragments in the stained sediment;
   (d) administering to the human a therapeutically effective amount of an antibiotic effective against the bacteria identified in step (c); and
   (e) monitoring the treatment by periodically repeating steps (a), (b) and (c) while continuing the treatment of step (d) until the performance of step (c) shows the substantial absence of the identified bacteria.

18. A method as defined in claim 17, wherein the antibiotic amount is at least 600 mg/day.

19. A method as defined in claim 17, wherein the antibiotic is selected from the group consisting essentially of clindamycin and lincomycin.

* * * * *